United States Patent
Zwart

(10) Patent No.: US 6,193,674 B1
(45) Date of Patent: Feb. 27, 2001

(54) BRUSH SUITABLE FOR TAKING A SMEAR

(75) Inventor: Meindert Durk Zwart, Rosmalen (NL)

(73) Assignee: MDZ Beheer B.V. (NL)

( * ) Notice: Subject to any disclaimer, the term of this patent is extended or adjusted under 35 U.S.C. 154(b) by 0 days.

(21) Appl. No.: 09/323,949

(22) Filed: Jun. 2, 1999

(30) Foreign Application Priority Data

Dec. 2, 1998 (NL) .................................................. 1010709

(51) Int. Cl.$^7$ .................................................. A61B 10/00
(52) U.S. Cl. .................................................. 600/569
(58) Field of Search .................. 600/569, 570, 600/562

(56) References Cited

U.S. PATENT DOCUMENTS

| | | | | |
|---|---|---|---|---|
| 3,881,464 | * | 5/1975 | Levene | 600/569 |
| 4,127,113 | * | 11/1978 | Nollan | 600/569 |
| 4,227,537 | * | 10/1980 | Suciu et al. | 600/569 |
| 4,759,376 | * | 7/1988 | Stormby | 600/569 |
| 4,762,133 | * | 8/1988 | Bayne et al. | 600/569 |
| 4,873,992 | * | 10/1989 | Bayne | 600/569 |
| 5,022,408 | * | 6/1991 | Mohajer | 600/569 |
| 5,191,899 | * | 3/1993 | Strickland et al. | 600/569 |
| 5,253,652 | * | 10/1993 | Fast | 600/569 |
| 5,370,128 | * | 12/1994 | Wainwright | 600/569 |
| 5,456,265 | * | 10/1995 | Yim | 600/569 |
| 5,623,941 | * | 4/1997 | Hedberg et al. | 600/569 |
| 5,713,369 | * | 2/1998 | Tao et al. | 600/569 |
| 5,738,109 | | 4/1998 | Parasher . | |
| 5,823,954 | | 10/1998 | Chaffringeon . | |

FOREIGN PATENT DOCUMENTS

| | | |
|---|---|---|
| 196 37 144 | 3/1998 | (DE) . |
| 0 412 610 | 2/1991 | (EP) . |
| 0 499 330 | 8/1992 | (EP) . |
| 2 366 826 | 5/1978 | (FR) . |
| 9100246 | 9/1992 | (NL) . |
| WO 89/10724 | 11/1989 | (WO) . |

\* cited by examiner

Primary Examiner—Max Hindenburg
Assistant Examiner—Brian Szmal
(74) Attorney, Agent, or Firm—Young & Thompson

(57) ABSTRACT

The invention relates to a brush suitable for taking a smear from the endocervical canal, comprising an elongated handle and a brush head placed on the handle, which brush head comprises a mandrel lying in line with the handle and brush hairs which run substantially parallel placed on the mandrel.

13 Claims, 2 Drawing Sheets

BRUSH SUITABLE FOR TAKING A SMEAR

BACKGROUND OF THE INVENTION

The invention relates to a brush which can be used to take a smear from the endocervical canal. In the current prior art such a smear is taken with, for example, the so-called cytobrush, put on the market by the company Medscand. The cytobrush is in the form of a woven metal wire, between which nylon hairs are woven on the front side. The nylon hairs are cut to the correct length with a blunt instrument, as a result of which there are often sharp ends on the hairs. A disadvantage of the woven metal wire is that said wire is stiff and can damage tissue if it is wrongly used.

When a smear is being taken, it is important for cells to be collected both from the outside of the cervix, the so-called ectocervical cells, and from the endocervical canal, the endocervical cells. Most abnormalities which can develop into cancer cells occur at the transition between these two areas. If the transition zone is situated far in, which is the case in, for example, older women, it is difficult to collect cell tissue from the transition zone. A specific endocervical sampler, such as the abovementioned Medscand cytobrush, is then used for this purpose.

U.S. Pat. No. 4,127,113 discloses a brush comprising an elongated handle and a brush head placed on the handle, which brush head comprises a mandrel lying in line with the handle, and brush hairs which run substantially parallel placed on the mandrel.

U.S. Pat. No. 4,759,376 discloses a brush which is in fact the same as the earlier so-called cytobrush. It is known from this document that the brush can have approximately 600 brush hairs with a thickness of approximately 0.06 mm. These brush hairs are placed in a helical pattern around the brush end of handle 4. The nylon brush hairs are wedged between two twisted wires and thereby acquire a radial position. The distance between adjacent brush hairs then decreases from the base towards the outside.

SUMMARY OF THE INVENTION

The object of the invention is to provide a brush suitable for taking a smear from the endocervical canal which is improved relative to the brushes known in the prior art.

The brush according to the invention is characterized in that the brush hairs are provided in finely distributed rows on the mandrel in such a way that capillary channels are present between adjacent brush hairs. The brush according to the invention has the advantage that it contains no rigid or stiff parts which could cause damage to tissue if the brush is not properly used.

According to a further advantageous embodiment, at least the brush head (which comprises the mandrel and brush hairs) is in the form of a one-piece plastic injection moulded product. The chance of hairs becoming detached from the mandrel is very minimal in that case.

Finely distributed rows of brush hairs according to the invention should be understood as meaning in particular brush hairs placed with a hair density of more than 400 hairs per $cm^2$. With such a high hair density, the brush is found to have a good cell-collecting action, so-called cell sampling. The cell sampling is found to be even better with a hair density of more than 600 hairs per $cm^2$. The cell sampling is found to be very good when there are more than 850 hairs per $cm^2$, such as more than 950 hairs per $cm^2$. The brush head comprising the mandrel and hairs is also easy to manufacture according to the invention as a one-piece plastic injection moulded product with a fineness of up to in any case 1000 to 1100 hairs per $cm^2$.

For good cell sampling, where on two substantially opposite longitudinal side parts the mandrel is provided with said brush hairs arranged in finely distributed rows, it has also been found advantageous for said brush hairs to run substantially parallel to each other on each longitudinal side part, transversely to the longitudinal direction of the mandrel. The term transversely should be understood in a general sense in this case as meaning at an angle which is greater than 45° relative to the longitudinal direction, more particularly at an angle which is greater than 70° relative to the longitudinal direction.

In order to permit the brush to be easily inserted into the endocervical canal even in the case of a narrow cervix, it is very advantageous according to the invention if the longitudinal faces of the mandrel situated between the opposite longitudinal side parts provided with brush hairs are free from brush hairs, in order to form an essentially flat brush head.

The brush according to the invention is preferably also provided with a stop in the transition area from the handle to the mandrel, in order to prevent the brush from being inserted too far. It is further desirable for at least the mandrel to be flexible. This makes the brush particularly suitable for use for sampling in a tilted uterus.

It has been found that the collecting action of the brush according to the invention is optimized by the specific positioning of the brush hairs as proposed by the invention.

The brush according to the invention is preferably manufactured from a single piece of flexible material, such as polyethylene. The hairs can then be designed as an integral part of the brush by being injection moulded at the same time on the mandrel. This also provides a shape for the brush and the hairs forming part of it which is repeatable and is determined by the shape of the mould, while undesirable sharp ends on the hairs are avoided.

The collecting action of the brush according to the invention can be further improved by designing it in such a way that the mandrel, viewed in cross-section, is formed as a polygon in which the mandrel has the same number of connecting flat faces running in the longitudinal direction of the mandrel as the number of angles of the polygon, and that at least one face, preferably at least two faces disposed substantially opposite each other, is provided—or are each provided—with brush hairs disposed in finely distributed rows, the brush hairs provided on one and the same face running substantially parallel to each other. Depending on the application, it is best if all faces are provided with brush hairs disposed in finely distributed rows.

In a preferred embodiment, the brush according to the invention is characterized in that the faces of the mandrel from the handle to the distal end of the mandrel are curved in such a way that the distal end of the mandrel has a cross-section measurement which is smaller than the measurement of the mandrel close to the handle. This means that the brush corresponds in the optimum manner to the shape of the particular body cavity for which the brush can be used.

The action of the capillary channels between the brush hairs is most effective if the brush hairs are all approximately the same length.

BRIEF DESCRIPTION OF THE DRAWINGS

The invention will now be explained on the basis of two non-limiting exemplary embodiments, with reference to the appended drawing, in which.

DESCRIPTION OF THE PREFERRED EMBODIMENTS

Figure 1:
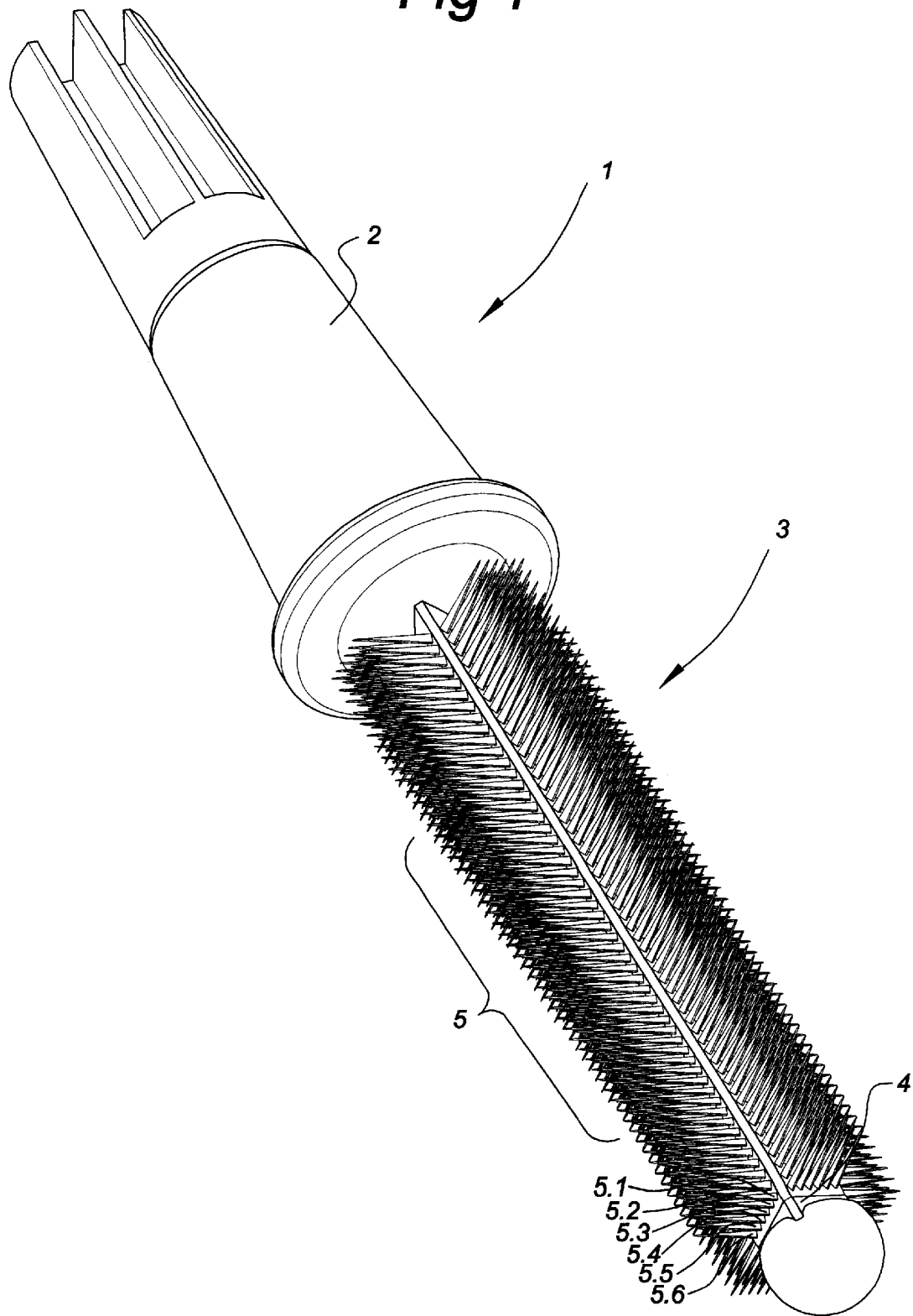
FIG. 1 shows a perspective view of a first exemplary embodiment of the brush according to the invention.

The brush 1 which is proposed by the invention and can be used for taking a smear from the endocervical canal comprises an elongated handle 2 and a brush head 3 which is placed on the handle and comprises a mandrel 4 lying in line with the handle 2 and brush hairs 5 which run substantially parallel placed on the mandrel 4. The brush hairs 5 are provided on the mandrel 4 in finely distributed rows 5.1, 5.2, 5.3, 5.4, 5.5, 5.6, in such a way that capillary channels are formed between adjacent brush hairs 5. In the context of the invention, adjacent brush hairs include not only the brush hairs disposed in the same row, but also the brush hairs disposed in different adjacent rows.

FIG. 1 shows the brush according to the invention in the embodiment in which the mandrel 4 is in the form of a polygon, in particular a square, with four mutually connecting flat faces running in the longitudinal direction of the mandrel 4 being present. Abovementioned finely distributed rows of brush hairs 5 are provided on all of these four faces. The brush hairs provided on different faces either lie in line with each other or are in a position perpendicular to the brush hairs 5 on other faces of the brush 1. What is essential for the invention is that capillary channels are formed between adjacent brush hairs 5. The brush hairs 5 are all approximately the same length, so that in each case capillary channels of approximately the same length are also formed. In the transition area from the handle 2 to the mandrel 4 a stop is also provided, in order to ensure that the brush 1 cannot be inserted too far.

The brush 1 according to the invention can be produced in a flexible material, for example polyethylene, which can be moulded to form the brush 1 by means of injection moulding, all separate parts of the brush 1 being connected to each other to form an integral unit. This is particularly desirable on account of the envisaged use of the brush; it ensures that material is not left behind in the body cavity which has been examined. By this measure it can also be ensured that the brush 1 in its entirety, but particularly the mandrel 4, is flexible, so that damage to tissue can be prevented as far as possible and body cavities in a difficult position can also be examined without problems. This applies in particular to the examination of a tilted uterus.

A variant of the brush 1 according to the invention which is not shown is characterized in that the faces of the mandrel from the handle to the distal end of the mandrel are curved in such a way that the distal end of the mandrel has a cross-section measurement which is smaller than the measurement of the mandrel near the handle.

Figure 2:
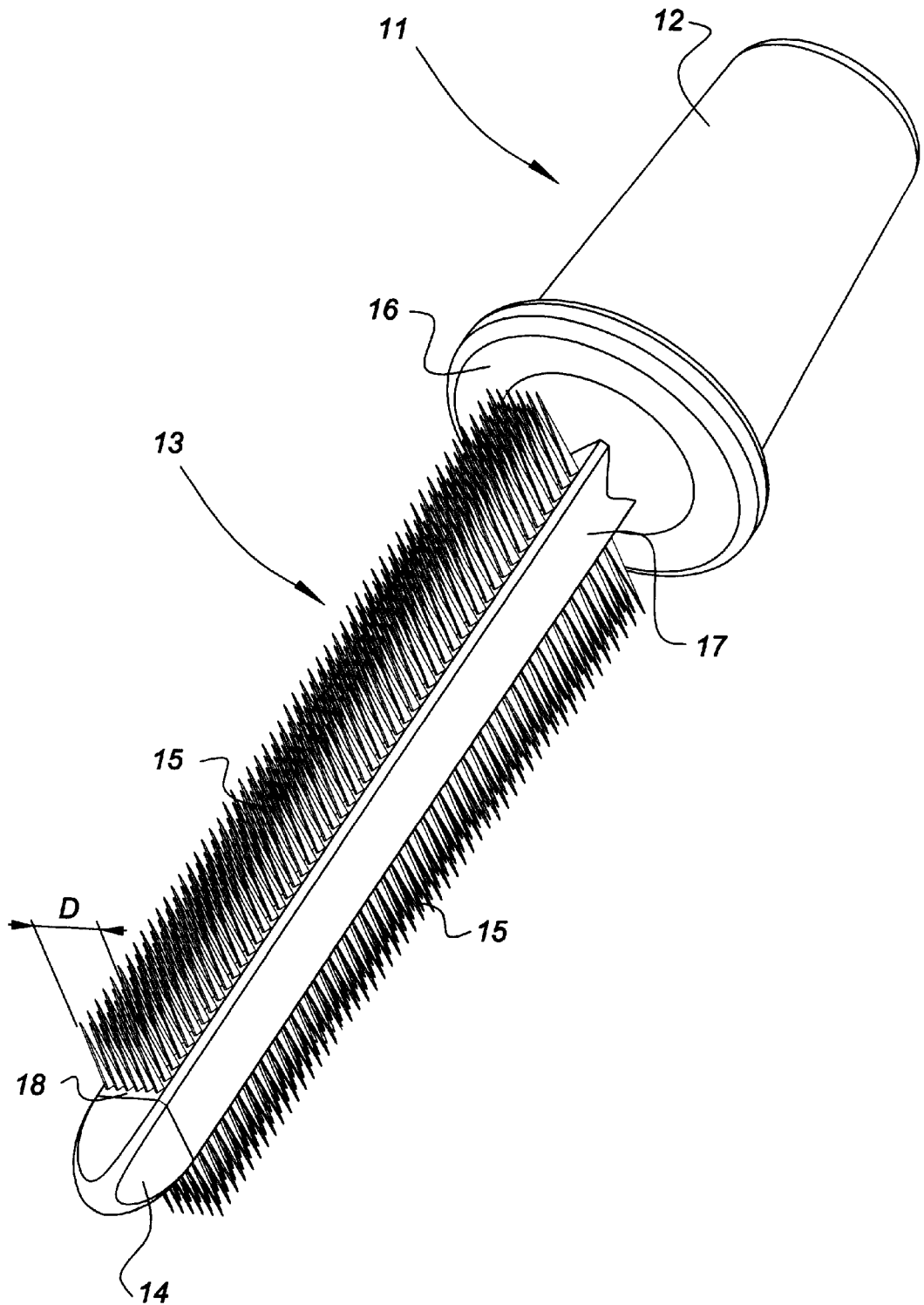
FIG. 2 shows a perspective view of a second exemplary embodiment of the brush according to the invention.

FIG. 2 shows a second embodiment of the brush according to the invention. In FIG. 2 the same reference numerals, increased by 10, are used for parts which correspond to those in FIG. 1.

The embodiment according to FIG. 2 is suitable in particular in the case of a narrow cervix, as quite often occurs in older women in particular and/or in the case of a slit-shaped cervix, as commonly found in the case of women who have borne a child. By providing only two opposite longitudinal side parts 18 with finely distributed rows of brush hairs 15 and keeping the longitudinal faces 17 of the mandrel 14 between these longitudinal side parts 18 free from brush hairs, it is possible to achieve a brush head which is relatively flat in the direction D. With six rows of brush hairs extending in the longitudinal direction of the mandrel 14 on each longitudinal side part 18, the thickness of the mandrel 14 in the direction D can be less than two millimetres.

In the case of the brush according to FIG. 2 the free front end of the mandrel 14 is designed by rounding in such a way that said end is no thicker than the mandrel itself, with the result that insertion into the cervix is facilitated. Although many methods of rounding are conceivable for that purpose and also lie within the scope of this invention, the rounding according to FIG. 2 is a parabolic shape. This parabolic rounding is also very suitable for use in the case of the brush from FIG. 1.

In order to clarify further the fineness of the brush according to the invention, the following values can be mentioned:

the thickness of the hairs on the mandrel will not exceed 0.2 to 0.3 mm at the root;

the length of the hairs will preferably not exceed 4 mm, and more preferably will be a maximum of 2 to 3 mm;

the density of the hairs will be at least 200 hairs per $cm^2$ and can vary over the length of the mandrel. The density of the hairs will preferably be greater than 400 hairs per $cm^2$.

In the case of the exemplary embodiments shown in FIGS. 1 and 2 the hairs have a mutual centre-to-centre spacing in the longitudinal direction of the mandrel of 0.35 to 0.4 mm, and in the transverse direction of the mandrel a centre-to-centre spacing of approximately 0.26 mm±0.02, the length of the hairs is approximately 2 mm±0.2, the thickness of the hairs at the root is approximately 0.2 to 0.3 mm, and the cross-section area of the hair at the root is approximately 0.09 to 0.11 mm. The density of the hair varies between 950 and 1075 hairs per $cm^2$, but can also very well be constant, for example approximately 1000 or approximately 1050 hairs per $cm^2$.

In the case of the exemplary embodiments shown, the brush hairs are situated substantially perpendicular to the longitudinal direction of the mandrel. However, it will be clear that the brush hairs need by no means be situated exactly perpendicular to said longitudinal direction. What is important is that they are directed substantially outwards relative to the longitudinal direction, or that they form an angle greater than 45° with the longitudinal direction, which angle will be greater than 70° in practice.

It is clear that the above description relates only to two non-limiting exemplary embodiments of the brush according to the invention, and that various variants are conceivable within the scope of the invention, all of them falling under the scope of protection of the following claims.

What is claimed is:

1. A brush suitable for taking a smear from a body cavity, comprising:

an elongated handle and a brush head on the handle, the brush head comprising a mandrel lying in line with the handle and having two substantially opposite longitudinal side parts provided with finely distributed rows of brush hairs, the brush hairs being substantially parallel to each other on each of the longitudinal side parts transversely to a longitudinal direction of the mandrel in such a way that capillary channels are present between adjacent ones of the brush hairs, the brush hairs having a density of at least 200 hairs per $cm^2$.

2. The brush according to claim 1, in which at least the brush head is in the form of a one-piece plastic injection molded product.

3. The brush according to claim 1, in which the brush hairs have a density of more than 400 hairs per $cm^2$.

4. The brush according to claim 1, in which the brush hairs have a density of more than 600 hairs per $cm^2$.

5. The brush according to claim 1, in which the brush hairs have a density of more than 850 hairs per $cm^2$.

6. The brush according to claim 1, wherein longitudinal faces of the mandrel situated between the opposite longitudinal side parts provided with brush hairs are free from brush hairs, in order to form an essentially flat brush head.

7. The brush according to claim 1, in which the mandrel, viewed in cross-section, is a polygon in which the mandrel has the same number of connecting flat faces running in the longitudinal direction of the mandrel as the number of angles of the polygon, and in which at least two of said flat faces disposed substantially opposite each other define said two substantially opposite longitudinal side parts provided with said finely distributed rows of brush hairs.

8. The brush according to claim 7, in which all said flat faces are provided with said finely distributed rows of brush hairs.

9. The brush according to claim 1, in which the faces of the mandrel from the handle to the distal end of the mandrel are curved in such a way that the distal end of the mandrel has a cross-section measurement which is smaller than the measurement of the mandrel near the handle.

10. The brush according to claim 1, in which a stop is provided in the transition area from the handle to the mandrel.

11. The brush according to claim 1, in which at least the mandrel is flexible.

12. The brush according to claim 1, comprising an orthogonal grid of the capillary channels, with a first set of the channels being substantially parallel to the longitudinal direction of the mandrel and a second set of the channels being substantially perpendicular thereto.

13. The brush according to claim 1, wherein the mandrel is generally square in cross section and in which four flat faces running in the longitudinal direction of the mandrel define two pairs of said two substantially opposite longitudinal side parts provided with the rows of brush hairs.

* * * * *